US008722386B2

(12) United States Patent
Reuter et al.

(10) Patent No.: US 8,722,386 B2
(45) **Date of Patent: *May 13, 2014**

(54) **COMPOSITIONS FOR STABILIZING *BACILLUS* SPORES AND METHODS OF USE THEREOF**

(75) Inventors: Christopher J. Reuter, Parrish, FL (US); Steven J. MacKenzie, Sarasota, FL (US)

(73) Assignee: Osprey Biotechnics, Inc., Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/925,371

(22) Filed: Oct. 20, 2010

(65) Prior Publication Data

US 2012/0100094 A1 Apr. 26, 2012

(51) Int. Cl.
*C12N 1/20* (2006.01)

(52) U.S. Cl.
USPC .......................................... 435/252.5; 424/76.6

(58) Field of Classification Search
CPC .............. C12N 1/04; C12N 1/20; C12N 1/38; C12N 3/00
See application file for complete search history.

(56) References Cited

U.S. PATENT DOCUMENTS

| | | | | |
|---|---|---|---|---|
| 3,720,606 | A * | 3/1973 | Horney et al. | ............... 424/76.8 |
| 4,798,723 | A | 1/1989 | Dart et al. | |
| 5,733,355 | A | 3/1998 | Hibino et al. | |
| 5,830,459 | A | 11/1998 | Cuero et al. | |
| 5,919,695 | A | 7/1999 | Vedamuthu et al. | |
| 5,935,843 | A | 8/1999 | Glendening et al. | |
| 6,423,310 | B1 | 7/2002 | Wilson et al. | |
| 6,541,607 | B1 | 4/2003 | Hansen | |
| 6,589,524 | B1 | 7/2003 | Douillet | |
| 6,974,691 | B2 * | 12/2005 | Fredenburgh et al. | ..... 435/262.5 |
| 7,358,076 | B2 | 4/2008 | Hansen | |
| 2004/0175407 | A1 | 9/2004 | McDaniel | |

FOREIGN PATENT DOCUMENTS

| | | | | |
|---|---|---|---|---|
| WO | WO 9946350 A1 * | 9/1999 | | |
| WO | WO 03/064755 * | 8/2003 | ............ | D06M 16/00 |

OTHER PUBLICATIONS

Wong et al., Effects of Lactic Acid Bacteria and Organic Acids on Growth and Germination of *Bacillus cereus*, 1988, Appl. Env. Microbiol. 54(9): 2179-2184.*
Rosenquist et al., The antimicrobial effect of organic acids, sour dough and nisin against *Bacillus subtilis* and *B. licheniformis* isolated from wheat bread, 1998, J. Applied Microbio. 85(3): 621-631.*
Waites WM, and Wild DG (1970), J. General Microbiology, 61:311-317.
Grossman AD, and Losick R (1988) Proc. Natl. Acad. Sci. USA, 85: 4369-4373.
Driks A (2002) Cellular and Mol. Life Sciences (2002) 59:389-391.

* cited by examiner

*Primary Examiner* — Jon P Weber
*Assistant Examiner* — Robert Yamasaki
(74) *Attorney, Agent, or Firm* — Butzel Long

(57) ABSTRACT

The invention provides methods for providing *Bacillus* spores for application to agricultural soil or plant material as well as zootechnic applications for odor control in areas of high ammonia generation. The methods comprise suspending the *Bacillus* spores in a liquid consisting of water and an organic acid, including acetic acid, wherein the acid lowers the pH so that the spores are inhibited from germination and growth; and so that growth of unwanted microorganisms in the suspension is prevented. Compositions formed according to the methods of the invention are also provided.

21 Claims, 1 Drawing Sheet

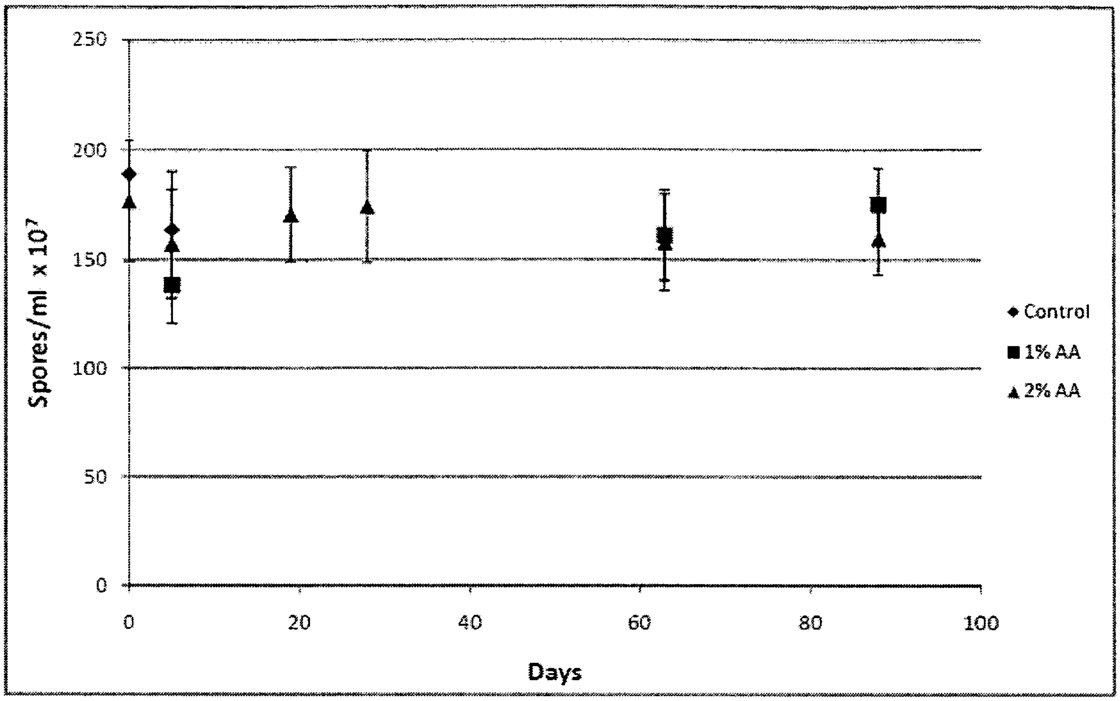
250
200
150
100
50
0
Spores/ml x 10^7
0
20
40
60
80
100
Days
Control
1% AA
2% AA

COMPOSITIONS FOR STABILIZING *BACILLUS* SPORES AND METHODS OF USE THEREOF

CROSS-REFERENCE TO RELATED APPLICATIONS

None.

STATEMENT REGARDING FEDERALLY SPONSORED RESEARCH OR DEVELOPMENT

None.

STATEMENT REGARDING GOVERNMENT RIGHTS

None.

FIELD OF THE INVENTION

The invention relates to methods and compositions for providing *Bacillus* spores in a liquid in which the germination and growth of the spores are inhibited, and spoilage is prevented. In various embodiments, the liquid consists essentially of water and acetic acid, preferably acetic acid from a fermentation.

BACKGROUND OF THE INVENTION

Bacterial cultures have wide industrial uses; including environmental and agricultural uses as bioremediation reagents, as alternatives to harmful chemicals such as certain pesticides, and as agents for improving plant and animal health. Industrial users of bacterial cultures include manufacturers of probiotics and prebiotics, bacterial seed coatings, and soil augmentation product manufacturers.

Particular species of the gram positive bacteria *Bacillus* have found uses in agriculture as antifungal agents. For example, U.S. Pat. No. 6,589,524 refers to the use of *B. cereus, B. amyloliquefaciens*, and *B. subtilis* for biological control of pathogenic fungi. U.S. Pat. No. 5,830,459 refers to application of *Bacillus*, including *B. subtilis* in combination with chitosanase inducers for preventing or treating microbial colonization and fungal growth. U.S. Pat. No. 6,423,310 refers to use of biological coatings that confer protective and curative effects for the control of postharvest decay. The coatings have antifungal properties and include chitosan salts, antagonistic organisms including yeast or bacteria such as *B. subtilis*, and a cation. Other uses of *Bacillus* have included uses of *Bacillus* preparations for soil conditioning, for enhancing fermentation of cellulosic materials, and as a deodorant for feces and urine of animals; as referred to in U.S. Pat. No. 5,733,355. U.S. Pat. No. 5,919,695 refers to an atypical *B. subtilis* strain for use in controlling molds and other spoilage flora in various materials, particularly foods.

Sporulation in gram positive bacteria, including *Bacillus*, leads to formation of spores (endospores) which are dormant; and therefore desirable for industrial purposes including manufacturing, shipping, and storage. Activation of the dormant spores leads to germination and growth of active bacteria. Sporulation in *B. subtilis* has been classically viewed as a unicellular differentiation that occurs in response to nutritional starvation. More recently, in addition to complex morphological and metabolic changes, changes in the soluble protein profile of the bacterium, including identification of specific proteins associated with sporulation have been reported. For example, the extracellular differentiation factor A (EDF-A), a secreted factor, is reported to be required, in addition to starvation conditions, for efficient sporulation in *B. subtilis*. See Waites W M, and Wild D G (1970), J. General Microbiology, 61: 311-317; Grossman A D, and Losick R (1988) Proc. Natl. Acad. Sci. USA, 85: 4369-4373; Driks A (2002) Cellular and Mol. Life Sciences 59: 389-391.

U.S. Pat. No. 5,935,843 to Glendening et al., the subject matter of which is incorporated herein in its entirety, discloses a method and apparatus for waste degradation. The method deposits microorganisms that degrade waste into waste traps typically found in restaurant settings. Before use, *Bacillus* or *Pseudomonas* microorganisms are freeze-dried, lypholized, or air-dried and can include a starch or sodium nitrate stabilizer to provide a longer life upon rehydration with water.

SUMMARY OF THE INVENTION

In one aspect, the invention provides a method for providing *Bacillus* spores for application to agricultural soil or plant material, which comprises the step: suspending the *Bacillus* spores in a liquid consisting essentially of water and acetic acid, wherein the acetic acid lowers the pH so that the spores are inhibited from germination and growth.

In a related aspect, the invention provides a method for providing a *Bacillus* on agricultural soil or plant material, which comprises the steps: (a) suspending *Bacillus* spores in a liquid consisting essentially of water and acetic acid, wherein the acetic acid lowers the pH so that the spores are inhibited from germination and growth; and (b) neutralizing the liquid of step (a) to enable the spores to provide an enabled *Bacillus* and applying the enabled *Bacillus* to the soil or plant material.

In another, the invention provides a method for providing a *Bacillus* on agricultural soil or plant material, which comprises the steps: (a) preparing *Bacillus* spores in a minimal media effective to sporulate *Bacillus*; (b) separating said spores from said media; (c) optionally washing said spores; (d) suspending the spores from step (b) or (c) in a liquid consisting essentially of water and acetic acid, wherein the acetic acid lowers the pH so that the spores are inhibited from germination and growth; and (e) neutralizing the liquid of step (d) to enable the spores to provide an enabled *Bacillus* and applying the enabled *Bacillus* to the soil or plant material.

In a further related aspect, the invention provides a composition comprising *Bacillus* spores suspended in a liquid at a pH from about 3.8 to about 4.2, said liquid consisting essentially of water and acetic acid derived from vinegar; wherein in use of the composition, the pH is raised and used for application to plant material or soil.

In another, the invention provides a composition comprising *Bacillus* spores in a liquid consisting essentially of water and acetic acid; wherein said composition is formed by the process comprising the steps: (a) preparing *Bacillus* spores in a minimal media effective to sporulate *Bacillus*; (b) separating said spores from said media; (c) optionally washing said spores; and (d) suspending the spores from step (b) or (c) in a liquid consisting essentially of water and acetic acid, wherein the acetic acid lowers the pH so that the spores are inhibited from germination and growth.

In another aspect, the invention provides a method for providing *Bacillus* spores for application to agricultural soil or plant material, which comprises the step: suspending the *Bacillus* spores in a liquid consisting essentially of water and an organic acid, wherein the organic acid lowers the pH so that the spores are inhibited from germination and growth. In particular embodiment, the method further comprises neutralizing the liquid of the suspending step to enable the spores to provide an enabled *Bacillus* and applying the enabled *Bacillus* to the soil or plant material. In another, the method further comprises the steps: i) preparing *Bacillus* spores in a minimal media effective to sporulate *Bacillus*; ii) separating said spores from said media; and iii) optionally washing said spores; wherein said steps (i), (ii), and (iii) are performed prior to the suspending step.

In another related aspect, the invention provides a composition comprising *Bacillus* spores in a liquid consisting essentially of water and an organic acid; wherein said composition is formed by the methods stated above.

In a further related aspect, the invention provides a method for providing *Bacillus* spores for application to agricultural soil or plant material, which comprises the steps: suspending the *Bacillus* spores in a liquid consisting essentially of water and an organic acid, wherein the organic acid lowers the pH so that the spores are inhibited from germination and growth; and transferring the suspension of the suspending step to a sealable container under aseptic conditions and sealing the container. In a particular embodiment, the method further comprises preparing *Bacillus* spores in a minimal media effective to sporulate *Bacillus*; separating said spores from said media; and optionally washing said spores prior to the suspending step. In another, the methods further comprise testing a sample of said suspension and thereby determining that the sample and the transferred suspension are acceptably free of unwanted microorganisms. In another, the unwanted organisms are selected from one or more of: coagulase positive *Staphylococcus* sp., *Pseudomonas aeruginosa, Salmonella/Shigella* sp., coliforms, yeast, and mold.

In another related aspect, the invention provides an article of manufacture comprising a sealed container comprising *Bacillus* spores in a liquid consisting essentially of water and an organic acid; wherein said article is formed by the methods stated above and comprising a transferring step. In a particular embodiment, the article further comprises directions for use wherein said directions comprise directing the user to neutralize the liquid in said container.

In another embodiment, the disclosure relates to a method for providing a *Bacillus* on a surface (in particular to remove ammonia from and/or otherwise deodorize the surface), the method comprising: (a) providing *Bacillus* spores suspended in a liquid consisting essentially of water and one or more organic acids (e.g., acetic acid), wherein the one or more organic acids lower the pH of the liquid (e.g., to about 3.8 to about 4.2) so that the *Bacillus* spores are inhibited from germination and growth; and; (b) applying the liquid of step (a) to a surface environment either containing ammonia or being capable of generating ammonia, wherein the ammonia neutralizes the one or more organic acids (e.g., neutralized to a pH from about 5 to about 10, about 5.5 to about 8.5, or about 7 to about 7.5)) to enable the *Bacillus* spores and provide an enabled *Bacillus* on the surface environment.

In another embodiment, the disclosure relates to a method for providing a *Bacillus* to deodorize an animal waste, the method comprising: (a) providing *Bacillus* spores suspended in a liquid consisting essentially of water and one or more organic acids (e.g., acetic acid), wherein the one or more organic acids lower the pH of the liquid (e.g., to about 3.8 to about 4.2) so that the spores are inhibited from germination and growth; and, (b) applying the liquid of step (a) to an animal waste selected from the group consisting of animal feces, animal urine, and combinations thereof, thereby deodorizing the animal waste (e.g., with the pH decrease resulting from the application of the low-pH liquid providing a means to immediately neutralize ammonia generated by or present in the animal waste and thereby activate/enable the inhibited *Bacillus* spores).

In another embodiment, the disclosure relates to an article of manufacture comprising: (a) a sealed container containing a composition comprising *Bacillus* spores suspended in a liquid at a pH from about 3.8 to about 4.2, said liquid consisting essentially of water and one or more organic acids, wherein: (i) the *Bacillus* spores are inhibited from germination and growth in the liquid; and (ii) in use of the composition, application of the liquid to a surface environment either containing ammonia or being capable of generating ammonia neutralizes the one or more organic acids and enables the *Bacillus* spores on the surface environment; and (b) directions for use of the composition, wherein the directions comprise directing a user to apply the liquid and suspended *Bacillus* spores in the container to a surface environment either containing ammonia or being capable of generating ammonia.

Various refinements of the foregoing methods and compositions are possible, in particular when used to remove ammonia from and/or otherwise deodorize a surface to which the compositions are applied. For example, the surface environment (e.g., a soil, solid/hard, or water surface) to which the composition/liquid is applied can comprise animal waste (e.g., human, non-human animal whether wild or domesticated as part of a zootechnic application) that further includes an ammonia-generating component. More particularly, the surface environment can be an animal enclosure (or part of the animal enclosure such as the ground or floor thereof) containing animal waste or being susceptible to accumulation of animal waste, the animal waste comprising an ammonia-generating component. (e.g., urine and/or feces containing urea, uric acid, or others). The animal enclosure can be closed to the external environment (e.g., a walled, covered building such as a coop, barn). Alternatively, the animal enclosure can be open to the external environment (e.g., an outside gated pen). The animal enclosure can house one or more domesticated animals selected from the group consisting of birds (e.g., poultry such as chickens), mammals (e.g., livestock such as cattle, pigs, sheep, horses), and combinations thereof. The surface environment can comprise at least one of a soil surface and a hard surface (e.g., wood, concrete) onto which the liquid in step (a) is applied, and optionally can comprise an animal bedding material (e.g., straw) on the soil surface or the hard surface.

In any aspect of the invention in which an organic acid is utilized, in a particular embodiment, the acid is acetic acid.

In any aspect of the invention comprising a suspending step, in a particular embodiment of the present invention, the pH in the suspending step is lowered to a pH from about 3.8 to about 4.2. In another, the acetic acid (or other acids) in said liquid in the suspending step is at a concentration of 1 to 5% or any amount suitable to obtain a desired pH. In another, the acetic acid is from a fermentation process to produce a vinegar used in the suspending step. In another, the acetic acid is from a 20 percent acetic acid vinegar which is used to lower the pH in the suspending step.

In any aspect of the invention comprising a preparing step, a suspending step, or in which the invention provides a composition comprising *Bacillus* spores, in a particular embodiment of the present invention, the *Bacillus* spores are *Bacillus subtilis* (e.g., ammonia-metabolizing *Bacillus subtilis*), for example additionally containing one or more ammonia-metabolizing *Bacillus* such as those selected from the group consisting of *Bacillus lichenformis, Bacillus pumilis*, and *Bacillus amyloliquefaciens.*

In any aspect of the invention in which the invention provides a method for providing *Bacillus* spores for application to agricultural soil or plant material, or in which the method provides an applying step, in a particular embodiment of the present invention, the plant material is a seed. In another, the applying is to soil. In another, the applying is to a plant.

In any aspect of the invention comprising a neutralizing step, in a particular embodiment of the present invention, the neutralizing is with a base, for example a base selected from the group consisting of: sodium bicarbonate, potassium bicarbonate, sodium hydroxide, potassium hydroxide, calcium carbonate, alkaline soil, sodium phosphate (dibasic salt), a glycine salt, and combinations thereof.

In any aspect of the invention comprising a separating step, in a particular embodiment of the present invention, the separating is by tangential flow filtration or centrifugation. In another, the tangential flow filtration utilizes a filter from about 0.1 micron to less than 1 micron. In another, the centrifugation is performed at a force from about 3000 g to about 10,000 g.

BRIEF DESCRIPTION OF THE DRAWINGS

FIG. 1 depicts a time course study of *Bacillus subtilis* spore suspensions prepared according to the methods of the invention.

DETAILED DESCRIPTION OF THE INVENTION

All patents, patent applications, government publications, government regulations, and literature references cited in this specification are hereby incorporated herein by reference in their entirety. In case of conflict, the present description, including definitions, will control.

Additional features of the disclosure may become apparent to those skilled in the art from a review of the following detailed description, taken in conjunction with the drawings, examples, and appended claims.

Preservation of dormant *Bacillus* spores desirable for industrial purposes can be achieved by methods such as drying, freeze-drying, lyophilization, and the like; where the spore preparations are not stored in a liquid. However; such methods have the disadvantages of additional effort and cost in preparing the non-liquid preparations; and also of being prone to additional opportunities for contamination. As an alternative, preservation of bacterial liquid products, in particular those containing *Bacillus* endospores, has long been achieved by addition of biostatic and/or biocidal agents; as a means of inhibiting undesired bacterial growth in the products. However, uses of such agents and other biologically harmful chemicals are not desired for applications including environmental, agricultural, food, and feed applications.

Therefore, non-synthetic (organic) methods of stabilization, and inhibition of unwanted microbial growth in *Bacillus* spore liquid cultures are useful for applications in which synthetic chemicals, particularly biologically harmful chemicals are not desired; including environmental, agricultural, food, and feed applications.

The invention is related to compositions and methods for stabilization of liquid *Bacillus* spore suspensions; preferably by using acetic acid from a fermentation source. The methods provide a means of both maintaining sporastatic conditions in *Bacillus* spore suspensions, as well as preventing spoilage of the liquid suspensions at ambient temperatures, including spoilage at room temperature. The sporastatic suspensions prepared according to the methods of the invention are useful for industrial applications, including environmental, agricultural, food, and feed applications; for example applications such as soil conditioning, antifungal treatment of plants, as a food or feed additive or preservative, and as a deodorant for feces and urine of animals.

An example of such a deodorizing application of the stabilized *Bacillus* spore composition includes application in zootechnic areas (including poultry, equine, swine, bovine, etc.) for the purpose of reducing problematic odors primarily produced from animal waste, including ammonia. The acidic stabilizer can prevent release of ammonia vapor for quick reduction of ammonia odors (e.g., via neutralization of the acid stabilizer with the ammonia, for example forming an ammonium organic acid salt such as ammonium acetate), while the bacterial portion of the composition can reduce remaining/re-occurring ammonia vapor through metabolism. Ammonia can be contained in or generated by animal waste such as urine and/or feces, either of which can contain ammonia itself or an ammonia precursor (e.g., urea, uric acid, and/or creatinine) that can convert to ammonia under typical environmental conditions (e.g., temperature and/or humidity conditions, with or without microbial action or other enzymatic breakdown). For example, urea, a component of urine (e.g., with urea accounting for about 97% of the urine's content), hydrolyzes in the presence of moisture to release ammonia, and the hydrolysis can be accelerated by microbial enzymatic processes (e.g., through the action of microbial urease). Similarly, fecal matter can contain a substantial amount of ammonia (e.g., approximately 50% ammonia), in particular for domesticated animals, which may have been fed a high-nitrogen diet, and whose waste can contain ammonia or nitrogen-containing precursors that generate ammonia upon microbial decomposition of the waste.

The acidic *Bacillus* suspension suitably is applied to a desired area with the expectation that ammonia generated by the animal waste would neutralize the acetic acid in the suspension, in which case the *Bacillus* spores would remain dormant until sufficient ammonia had been generated by the waste. This provides a synergistic combination of ammonia-reducing effects, insofar as the *Bacillus* remains dormant while it is not needed to reduce ammonia (i.e., because of the presence of neutralizable organic acid), and the *Bacillus* becomes enabled when it is needed to reduce ammonia (i.e., because the organic acid is completely or substantially neutralized and can no longer substantially reduce ammonia). The presence of ammonia can be a pre-existing condition at the time of suspension application, for example based on the presence of untreated animal waste for a sufficient time prior to application. Alternatively, the suspension can be applied as a preventative to an area that is initially free/substantially free of animal waste or ammonia, yet which is expected to accumulate animal waste or ammonia at some point after application. Thus, the relative time at which the dormant *Bacillus* spores become enabled after application varies with the initial amount and generation rate of ammonia in the applied area. In some cases, when the initial amount of present ammonia is low and/or the expected generation rate of ammonia is low, it may be desirable to partially neutralize the *Bacillus* suspension (e.g., to a low, yet spore-enabling pH of about 5-6 or 5-7) so that the spores can begin their metabolic activity while the composition retains some acidity capable of neutralizing further ammonia. Such partial neutralization can be performed by adding a neutralizing base to the suspension prior to application or by buffering the suspension (e.g., to a pH of about 5-6 or 5-7, for example including sodium, alkali metal, or other salts of the organic acid(s) or common buffer systems such as bicarbonate, phosphate, etc.) prior to application. Additionally, denitrification and sulfate reduction are other microbial processes that could serve to neutralize or alkalinize the environment in addition to hydrolysis of urea to form ammonia. Uric acid (e.g., variously a component of urine or feces depending on the animal species) is a weaker acid than acetic acid and also could contribute to neutralization of the acetic acid.

Settings for the zootechnic application of the *Bacillus* suspension to control odor are not particularly limited and generally include any surface environment either already containing ammonia or being capable of generating ammonia (e.g., being susceptible to the accumulation of animal waste containing ammonia-generating compounds such as urea). The specific setting can include enclosed or open areas where volatile ammonia odor is considered a nuisance, in particular areas in which there is some accumulation of moisture. Example indoor settings include animal housings such as barns and chicken coops. Outdoor settings can include gated animal pens or waste holding areas such as waste holding pits (e.g., situated beneath or adjacent to a facility in which animals are housed), lagoons, waste wetlands, and waste holding tanks (e.g., open or closed tanks to hold animal waste from zootechnic applications). Outdoor settings can further include areas where human waste accumulates (e.g., animal waste from a non-zootechnic application), for example in holding/storage tanks or other unit operations in waste water treatment facilities and outdoor/temporary toilet installations, or where non-human animal waste accumulates naturally (e.g., not from a zootechnic application). The types of animal enclosures/animal wastes that can be targeted with the composition are not particularly limited, but common examples of domesticated animals capable of generating substantial ammonia odors include various birds (e.g., poultry such as chickens) and mammals (e.g., livestock such as cattle, pigs, sheep, horses). Similarly, the particular surface to which the composition is applied is not particularly limited, and it generally includes any surface where waste accumulates such as soil/ground or a hard surface (e.g., wood, concrete), either of which may contain a bedding material such as straw, and/or water (e.g., an artificial or natural standing body of water where waste is stored or accumulates).

For the purposes of the invention, as used herein, by "sporastatic conditions" is meant conditions that determinably prevent and/or inhibit germination and growth of the spores into enabled *Bacillus*; by "enabled *Bacillus*" is meant non-dormant *Bacillus* capable of germination and growth to a vegetative state; by "spoilage" is meant growth of unwanted microorganisms. For the purposes of the invention, as used herein, the term "plant" includes seeds or any growing portion of a higher plant, including, for example, roots, shoots, leaves, and the like. For the purposes of the invention, as used herein, the term "plant material" includes any material derived or harvested from a plant, including for example, leaves, roots, shoots, fruit, seeds, and the like; as well as foods and feeds.

Particular embodiments of the invention comprise suspending *Bacillus* spores in a liquid consisting essentially of water and one or more organic acids (e.g., acetic acid), wherein the organic acid lowers the pH so that the spores are inhibited from germination and growth, as stated above. Additional, optional ingredients that do not alter the sporastatic nature of the suspension can be added to the composition, for example including one or more pH buffer components (as described above) and/or one or more acid-stable rheology modifiers to maintain the dormant *Bacillus* spores stably suspended in the liquid medium. Examples of suitable acid-stable rheology modifiers include natural gums/polysaccharides such as xanthan gum and guar gum as well as acid-swellable acrylate thickeners such as CARBOPOL AQUA CC (available from Lubrizol Corporation, Wickliffe, Ohio). It is recognized that the particular order of combining water, organic acid, and the spores, is not limiting, so long as the stated lowering of the pH, and/or concentration of the organic acid is achieved. For example, the invention encompasses preparing a desired dilution of organic acid by combining organic acid and water, and thereafter combining the spores with the diluted organic acid. Alternatively, the spores can be combined with water to produce a suspension and a desired amount of concentrated organic acid added to the suspension. Regardless of the particular order, the pH can be monitored as needed, including the pH of the final sporastatic spore suspension.

It is envisioned that the sporastatic suspensions comprising the *Bacillus* spores are suitable for storage at ambient temperatures, including room temperature. The shelf life of the suspensions can be determined by methods well known in the art, and as otherwise illustrated or described herein; such as by visual inspection for gross contamination; microscopic examination to determine spoilage such as unwanted bacterial, fungal, yeast or mold growth; microscopic examination to confirm maintenance of spores (i.e. confirmation of inhibition of continued inhibition of germination and growth), and specific assays to determine contamination by other unwanted bacteria, such as gram negative bacteria, and the like. In this regard, the compositions prepared according to the methods of the invention are stable for at least 3 months, six months, one year, and even up to two years from the time of their preparation, when stored at ambient temperatures, including room temperature.

It is recognized that for the purposes of commercial preparation, storage, and/or shelf life study, it is desirable to store the compositions prepared according to the methods of the invention in a sealed container, such as a sealed vessel, a drum, and the like. Thus, in a particular embodiment of the invention, the methods of the invention further comprise sealing a container containing the *Bacillus* spores suspended in a suspension step according to the methods of the invention. In another, the invention encompasses an article of manufacture comprising the sealed container. In another, the article includes directions for use. In another, the directions comprise directions for neutralizing the liquid in said container.

Particular embodiments of the present invention utilize acetic acid from a fermentation process to produce a vinegar. In further embodiments, the acetic acid is from a 20 percent acetic acid vinegar. It is recognized that an advantage of the present invention is the utilization of non-synthetic sources of acetic acid; in other words, acetic acid derived from a fermentation process, rather than a chemical synthesis process. Suitable industrial vinegar preparations for use in the methods and compositions of the invention include, for example, Distilled White Vinegar Concentrate (national Vinegar Co., St Louis Mo.; Product NO. nvc-5034) which is available as a 20% (200 g/l) concentrate.

Other acids suitable for the purposes of the methods and compositions of the invention include other water soluble organic acids. Preferably such water soluble organic acids have a carbon chain length of ten or less; or seven or less. Examples of such suitable organic acids include lactic-, citric-, succinic-, malic-, and formic acid, and the like. It is recognized that the suitable organic acid for the purposes of the invention be of a chain length to have favorable solubility in water, for the purposes of the invention. A particular acid suitable for use in the methods and compositions of the invention is lactic acid, which is well known to be producible by non-synthetic means from lactic acid producing bacteria, including lactobacilli and/or *Pediococcus* which are well known as being suitable for food applications. In particular embodiments of the invention, one or more suitable organic acids are substituted for, or used in combination with acetic acid according to the methods of the invention. Such suitable organic acids are non-toxic for the purposes of the invention; with respect to the bacterial spores and with respect to the particular intended application.

In an aspect of the invention comprising a neutralizing step, in a particular embodiment of the present invention, the neutralizing is with a base, for example a base selected from the group consisting of: sodium bicarbonate, potassium bicarbonate, sodium hydroxide, potassium hydroxide, calcium carbonate, sodium phosphate (dibasic salt), a glycine salt (e.g., alkali metal salt), ammonia (e.g., generated by or contained in animal waste such as animal feces or urine), and alkaline soil. As stated herein, the neutralizing is to enable the *Bacillus* spores to provide an enabled *Bacillus* for application to agricultural soil or plant material. In particular embodiments of the present invention, the methods further comprise applying the enabled *Bacillus* to the soil or plant material. Thus, it is recognized that where the application is to alkaline soil, the neutralizing and the applying steps can be optionally, and conveniently, combined. In other words, where the soil is of sufficient alkalinity to neutralize the acidic liquid in which the sporastatic spores are suspended, the neutralizing of the acidic suspension liquid can be achieved by direct application of the spores suspended according to a suspending step of the invention to the alkaline soil; thereby neutralizing the liquid and providing an enabled *Bacillus* to the soil in the same step. For the purposes of the invention, a pH range of about 5-10 or about 5.5-8.5 is considered as being sufficiently neutral for most applications requiring a neutral pH, with the pH of about 7.0-7.5 being optimal; however, it is recognized that the pH can be optimized in a strain-specific manner depending upon the particular *Bacillus* strain and the type of application desired. The invention encompasses all variations of the neutralizing step that bring about an enabled *Bacillus* for application to soil, plant or plant material.

In any aspect of the invention comprising an optional washing step, the washing is achieved by utilization of water, or an organic acid diluted for the purposes of washing, including for example acetic acid diluted for use in a suspending step of the invention. The particular choice of the wash liquid, the manner and number of washes can be optimized by the ordinarily skilled artisan, for the purposes of the invention.

*Bacillus* species particularly suitable for the purposes of the methods and compositions of the invention include the *B. subtilis, B. amyloliquefaciens, B. atropheus, B. mojavensis*, and *B. spizizenii*; and the invention encompasses particular embodiments in which the *Bacillus* is selected from one or more of these species. Depending on the particular application desired, other such suitable species of *Bacillus* include non-pathogenic *B. megaterium, B. pumilus, B. simplex, B. licheniformis, B. sonorensis, B. vietnamensis, B. acidicola, B. oleronius*, and *B. cereus, B. circulans, B. polymyxa, B. coagulans*, and *B. macetans*. The particular species and/or strains selected are non-pathogenic for the purposes of the particular application; and include natural and/or modified strains. For the purposes of the invention, as used herein, by "modified" is intended a strain harboring a plasmid, or recombinant strains in which heterologous nucleic acid is integrated into the bacterial genome by recombinant methods.

In addition to the ammonia-neutralizing effect of the stabilizing acid component in the *Bacillus* suspension, the particular *Bacillus* species used for the zootechnic application reduces ammonia (either pre-existing or newly generated) through metabolism. Example metabolic mechanisms include assimilation, nitrification (i.e., ammonia oxidation), and denitrification (i.e., removal of nitrogen in the form of $N_2$). Denitrification generally proceeds via reduction of nitrate or nitrite, although under anaerobic conditions ammonia can be oxidized to $N_2$. Assimilation can proceed via uptake of ammonia after urea or uric acid hydrolysis by another microbe, or, alternatively or additionally, the applied *Bacillus* sp. may catalyze these hydrolysis reactions, for example by producing relevant enzymes. Examples of *Bacillus* species that produce urease include *B. cereus, B. pasteurii* and *B. subtilis*. Examples of species that produce uricase include *B. subtilis, B. uricase* and *B. fastidiosus. Bacillus*, being a heterotroph, has the ability to assimilate nitrogen resulting from the catalytic breakdown of such nitrogen-containing molecules. *Bacillus* species with the ability to oxidize ammonia include *B. subtilis, B. cereus*, and *B. lichenifonnis*, and, in some instances, such species also can have the ability to denitrify. Suitable species for odor control include various combinations of *B. subtilus, B. licheniformis, B. pumilis*, and *B. amyloliquefaciens*, which species can have multiple pathways for ammonia metabolism.

In addition to ammonia control, *Bacillus* in a zootechnic application additionally could be used to inhibit bacterial pathogens and insects. Various *Bacillus* species with antibiotic properties are known. For example, *B. subtilis, B. pumilus, B. licheniformis, B. clausii, B. megaterium*, and *B. firmus* displayed antimicrobial activity against other *Bacilli* and bacteria of the genera *Clostridium, Staphlococcus* and *Listeria. B. thuringiensis* strains are effective against a broad spectrum of insects and some strains have shown nematicide activity. Strains of *B. penetrans* and *B. fermis* also have displayed nematicide activity, and both species infect plant parasitic nematodes. *B. polymyxa, B. subtilis* and *B. licheniformis* have displayed activity against fungi.

The invention provides methods for providing *Bacillus* spores for application to agricultural soil or plant material, and particular embodiments of the invention comprise applying the enabled *Bacillus* to the soil or plant material. The application is achieved by any method known to the ordinarily skilled artisan to bring an effective amount of the *Bacillus* spores into contact with the plant, plant material or soil, for the intended purpose of the application. For example, for field applications, the applying can be achieved by spraying, by conducting foliar spray, and the like. Examples of known methods that can be utilized in an applying step of the invention include those described in U.S. Pat. No. 6,589,524; U.S. Pat. No. 5,830,459; and U.S. Pat. No. 6,423,310 for antimicrobial and anti fungal purposes; in U.S. Pat. No. 5,733,355 for soil application purposes; and U.S. Pat. No. 5,919,695 for the purposes of mold control and prevention of spoilage in various materials including foods; the contents of each recited patent is hereby incorporated herein by reference.

The following illustrations are provided by way of example and are not meant to be construed as limiting the invention. Unless otherwise indicated, all numerical ranges provided in the present description are inclusive of the endpoints, and of all numerical values between the endpoints.

EXAMPLES

Example 1

Dry Spore Preparation Characteristics

Where needed for commencing liquid cultures, a dry preparation of *Bacillus* spores having a typical spore count of $100\times10^9$ spores/g is tested for, and found to be free of coagulase positive *staphylococcus, Pseudomonas aeruginosa*, and *Salmonella/Shigella* sp. The preparation is further tested for the presence of yeast and mold, by plating on Potato Dextrose Agar (PDA) and found to contain less than 100 spores/g. The preparation is further tested for the presence of coliforms by plating on Hektoen agar and found to contain less than 100 colony forming units (cfu)/g.

Example 2

Enumeration Procedure

Enumeration of the liquid spore suspensions was performed according to the following procedure. The suspension was distributed to three VWR 1 Liter glass bottles and labeled as Control, 1% Acetic Acid, and 2% Acetic Acid. To create each of the test spore suspensions, an OMRI listed 20% non-synthetic Acetic Acid (nsAA) (National Vinegar Company) was utilized. Before samples were taken, the three containers were shaken vigorously for five minutes using arc-like swings assuring that no precipitate was seen in the bottles. Using a 1 ml sterile pipette, 1 ml was transferred from the spore suspension to a 99 ml dilution buffer bottle labeled $10^{-2}$. Repeatedly, the 1 ml pipette was rinsed with the $10^{-2}$ dilution buffer until the sample was completely removed from the pipette. The $10^{-2}$ dilution bottle was shaken vigorously for one minute using the arm in an arc-like motion. Using another sterile pipette, 1 ml was transferred from the $10^{-2}$ bottle to a 99 ml dilution buffer bottle labeled $10^{-4}$. Repeatedly, the 1 ml pipette was rinsed with the $10^{-4}$ dilution buffer until the sample was completely removed from the pipette. For $10^{-7}$ plating, using an 11 ml sterile pipette, 11 ml was transferred from the $10^{-5}$ bottle to a 99 ml dilution buffer bottle labeled $10^{-6}$. The $10^{-6}$ dilution bottle was vigorously shaken for one minute using the arm in an arc-like motion as described. Using a calibrated micropipette, 100 µl from $10^{-6}$ dilution bottle was transferred onto four dry Trypticase Soy Agar (TSA) plates. All plates were incubated at 37° C. and counted after 24 hours of incubation. The counts are reported as spores per milliliter (spores/ml). All three samples were struck for isolation on Hektoen and MacConkey agar at 35° C. and 25° C. respectively for 48 hours, to serve as an indicator of unwanted growth in the spore suspensions. As gram positive organisms, such as members of the Genus *Bacillus*, are incapable of growth on these selective media, presence of any growth indicates inefficient stabilization.

Example 3

Preparation and Testing of *Bacillus Subtilis* Spore Suspensions

*Bacillus subtilis* spores were prepared in a stainless steel bioreactor using a minimal media for spore production*, as is well known in the art. Media was autoclaved at 121° C. for 30 minutes prior to inoculation. Seed culture was inoculated at 1%, incubated at 35° C. and agitated at 250 rpm under aeration for 24-72 hours. Samples were examined microscopically over this period to detect the formation of endospores. When 90-100% sporulation was visually detected, typically corresponding to $5\times10^8$ to $5\times10^{10}$ spores/ml, the spore broth was concentrated via tangential flow microfiltration using a Millipore Pellicon system (Millipore Corporation, Billerica, Mass.) with a 0.1 micron Pellicon 2 mini filter (cat. # P2B01MV01). Typically, the microfiltration was continued until the concentration of the spores in the medium was about 8-10 times in comparison to the spore concentration in the beginning of the filtration. The resulting spore slurry, was divided into three non-sterile vessels labeled Control, 1% nsAA (non-synthetic Acetic Acid), and 2% nsAA. An OMRI (Organic Materials Review Institute)—listed 20% nsAA (National Vinegar Company) was respectively added to create each of test spore suspensions, while de-ionized water was used to make up the volume difference in the control and test suspensions. Typically, the spores were suspended in the indicated concentrations of acetic acid to a final count of $1\times10^9$ to $1\times10^{11}$ spores/ml. All three samples were enumerated using the enumeration procedure set forth above, and struck for isolation on Hektoen and MacConkey agars, incubated at 35° C. and 25° C. respectively, to serve as an indicator of unwanted growth in the spore suspensions. As gram positive organisms, such as members of the Genus *Bacillus*, are incapable of growth on these selective media, presence of any growth indicates inefficient inhibition of unwanted microbial growth.

The results depicted in FIG. 1 indicate that under the conditions tested, the spore suspensions suspended in 1% or 2% nsAA are stable for at least 88 days. Plating of the samples on Hektoen-, MacConkey, and Potato Dextrose agar plates as explained above, indicates that the spore preparations in 1% or 2% nsAA are free of unwanted microorganisms.

*Minimal Media for Spore Production (Percentages Represent Weight/Volume):

0.1-2% D-Monosaccharide (Dextrose, D-Fructose, D-Mannose, or D-Galactose); or sucrose or starch 0.1-2% Yeast Extract 0.1-2% Vegetable Peptone (soy, wheat, or pea); or Corn Steep Liquor 0.5% Sodium or potassium salt (NaCl, KCl, NaBr, or KBr)

0.01-0.05% Each of $Mg^{++}$; $Mn^{++}$; $Ca^{++}$; $Fe^{++}$; and $Zn^{++}$ salts ($MgCl_2$, $MnCl_2$, $CaCl_2$, $FeSO_4$, $ZnSO_4$)

Examples 4-11

Application of *Bacillus* Spore Suspensions for Odor Control

The acetic acid-inhibited *Bacillus subtilis* spore suspension of Example 3 (or other *Bacillus*/organic acid combination) is used to control odor in a variety of settings, in particular where odor is generated by ammonia and/or animal waste. As in Example 3, the *Bacillus* suspension conveniently contains about $10^9$ spores/ml to about $10^{11}$ spores/ml (or more broadly at least about $10^7$, $10^8$, or $10^9$ spores/ml and/or up to about $10^{10}$, $10^{11}$, or $10^{12}$ spores/ml, for example about $10^7$ spores/ml to about $10^{10}$ spores/ml, depending on the desired application). The acid-stabilized, dormant *Bacillus* spore suspension is stored at room/ambient temperature (about 50° F. to 90° F., about 60° F. to 80° F., or about 70° F.) until needed for use, in particular in a sealed container for extended periods of up to 3, 6, 12, or 24 months without substantial loss of activity. Upon use, the *Bacillus* spore suspension is applied directly to the area of interest. Analogous to the methods above for application to agricultural material such as plants or soil, the application of the *Bacillus* spore suspension is achieved by any method known to the ordinarily skilled artisan to bring an effective amount of the spores into contact with the target area, in particular by spraying. As described in the specific examples below, the *Bacillus* spore suspension in some embodiments is applied to the area of interest at a spore concentration substantially the same at that of the stored, acid-inhibited suspension prior to use, in particular if the initial spore concentration is suitable for the area (i.e., based on an estimated level of desired *Bacillus* activity given the level of odor or amount of odor-generating constituents in the area). In other embodiments, the suspension is diluted before application with any of a variety of aqueous-based liquids, for example when a lower level of *Bacillus* activity is desired in the area of interest. Whether diluted or applied directly from the spore concentrate, the suspension is conveniently applied at a surface application rate of about 1 gallon/1000 $ft^2$ (e.g., about 0.1 gal-10 gal, 0.2 gal-5 gal, or 0.5 gal-2 gal per 1000 $ft^2$, for example at a concentration sufficient to apply at least about $10^6$ or $10^7$ spores/$ft^2$ and/or up to about $10^9$ or $10^{10}$ spores/$ft^2$ to the surface) to ensure substantially even, homogeneous coverage of the applied suspension (e.g., in terms of the local spore and acid concentration over the applied area).

Example 4

In an embodiment, the target area of application is in need of a high level of *Bacillus* activity, and the concentrated *Bacillus* suspension containing about $10^9$ spores/ml to about $10^{11}$ spores/ml (or at least about $10^7$, $10^8$, or $10^9$ spores/ml and/or up to about $10^{10}$, $10^{11}$, or $10^{12}$ spores/ml, for example about $10^7$ spores/ml to about $10^{10}$ spores/ml) is removed from storage and is sprayed directly on surfaces in the area of interest at a surface application rate of about 1 gallon/1000 $ft^2$ (for example at a concentration sufficient to apply at least about $10^6$ or $10^7$ spores/$ft^2$ and/or up to about $10^9$ or $10^{10}$ spores/$ft^2$ to the surface).

Example 5

In another embodiment, the target area of application is in need of a relatively lower level of *Bacillus* activity, and the concentrated *Bacillus* suspension containing about $10^9$ spores/ml to about $10^{11}$ spores/ml (or at least about $10^7$, $10^8$, or $10^9$ spores/ml and/or up to about $10^{10}$, $10^{11}$, or $10^{12}$ spores/ml, for example about $10^7$ spores/ml to about $10^{10}$ spores/ml) is removed from storage and diluted with water (e.g., tap, well, distilled, or deionized) by a factor of about 10 to about 1000. The diluted *Bacillus* suspension is then sprayed directly on surfaces in the area of interest at a surface application rate of about 1 gallon/1000 $ft^2$ (for example at a concentration sufficient to apply at least about $10^6$ or $10^7$ spores/$ft^2$ and/or up to about $10^9$ or $10^{10}$ spores/$ft^2$ to the surface).

Example 6

In another embodiment, the target area of application is in need of a relatively lower level of *Bacillus* activity (i.e., similar to Example 5), and the concentrated *Bacillus* suspension containing about $10^9$ spores/ml to about $10^{11}$ spores/ml (or at least about $10^7$, $10^8$, or $10^9$ spores/ml and/or up to about $10^{10}$, $10^{11}$, or $10^{12}$ spores/ml, for example about $10^7$ spores/ml to about $10^{10}$ spores/ml) is removed from storage and is diluted by a factor of about 10 to about 1000. In this embodiment, however, the concentrated *Bacillus* suspension is diluted with an aqueous solution including a base in order to provide less acid-ammonia neutralization capacity (i.e., based on the at least partial neutralization of the acids present for preservation) relative to *Bacillus* activity and to accelerate the activation of the dormant *Bacillus* spores in the suspension. The base-diluted *Bacillus* suspension is then sprayed directly on surfaces in the area of interest at a surface application rate of about 1 gallon/1000 $ft^2$ (for example at a concentration sufficient to apply at least about $10^6$ or $10^7$ spores/$ft^2$ and/or up to about $10^9$ or $10^{10}$ spores/$ft^2$ to the surface).

Example 7

In another embodiment, the target area of application is in need of a relatively lower level of *Bacillus* activity (i.e., similar to Examples 5 and 6), and the concentrated *Bacillus* suspension containing about $10^9$ spores/ml to about $10^{11}$ spores/ml (or at least about $10^7$, $10^8$, or $10^9$ spores/ml and/or up to about $10^{10}$, $10^{11}$, or $10^{12}$ spores/ml, for example about $10^7$ spores/ml to about $10^{10}$ spores/ml) is removed from storage and is diluted by a factor of about 10 to about 1000. In this embodiment, however, the concentrated *Bacillus* suspension is diluted with an aqueous solution containing an acid (e.g., one or more organic acids that are the same or different from that/those used in the spore concentrate) in order to provide more acid-ammonia neutralization capacity relative to *Bacillus* activity. The acid-diluted *Bacillus* suspension is then sprayed directly on surfaces in the area of interest at a surface application rate of about 1 gallon/1000 $ft^2$ (for example at a concentration sufficient to apply at least about $10^6$ or $10^7$ spores/$ft^2$ and/or up to about $10^9$ or $10^{10}$ spores/$ft^2$ to the surface).

Example 8

In another embodiment, the target area of application is in need of a relatively lower level of *Bacillus* activity (i.e., similar to Examples 5 to 7), and the concentrated *Bacillus* suspension containing about $10^9$ spores/ml to about $10^{11}$ spores/ml (or at least about $10^7$, $10^8$, or $10^9$ spores/ml and/or up to about $10^{10}$, $10^{11}$, or $10^{12}$ spores/ml, for example about $10^7$ spores/ml to about $10^{10}$ spores/ml) is removed from storage and is diluted by a factor of about 10 to about 1000. In this embodiment, however, the concentrated *Bacillus* suspension is diluted with an aqueous buffer solution in order to provide more acid-ammonia neutralization capacity relative to *Bacillus* activity. The buffer-diluted *Bacillus* suspension is then sprayed directly on surfaces in the area of interest at a surface application rate of about 1 gallon/1000 $ft^2$ (for example at a concentration sufficient to apply at least about $10^6$ or $10^7$ spores/$ft^2$ and/or up to about $10^9$ or $10^{10}$ spores/$ft^2$ to the surface).

Example 9

In another embodiment, the target area of application is in need of a high level of *Bacillus* activity (i.e., similar to Example 4), and the concentrated *Bacillus* suspension containing about $10^9$ spores/ml to about $10^{11}$ spores/ml (or at least about $10^7$, $10^8$, or $10^9$ spores/ml and/or up to about $10^{10}$, $10^{11}$, or $10^{12}$ spores/ml, for example about $10^7$ spores/ml to about $10^{10}$ spores/ml) is removed from storage for use substantially at its stored concentration. In this embodiment, however, a concentrated base (e.g., a solid base salt or a highly concentrated aqueous base solution) is added the concentrated *Bacillus* suspension to provide less acid-ammonia neutralization capacity (i.e., based on the at least partial neutralization of the acids present for preservation) relative to *Bacillus* activity and to accelerate the activation of the dormant *Bacillus* spores in the suspension (i.e., similar to Example 6) without substantially diluting the concentrated *Bacillus* suspension. The at least partially neutralized, concentrated *Bacillus* suspension is then sprayed directly on surfaces in the area of interest at a surface application rate of about 1 gallon/1000 $ft^2$ (for example at a concentration sufficient to apply at least about $10^6$ or $10^7$ spores/$ft^2$ and/or up to about $10^9$ or $10^{10}$ spores/$ft^2$ to the surface).

Example 10

In another embodiment, the target area of application is in need of a high level of *Bacillus* activity (i.e., similar to Example 4), and the concentrated *Bacillus* suspension containing about $10^9$ spores/ml to about $10^{11}$ spores/ml (or at least about $10^7$, $10^8$, or $10^9$ spores/ml and/or up to about $10^{10}$, $10^{11}$, or $10^{12}$ spores/ml, for example about $10^7$ spores/ml to about $10^{10}$ spores/ml) is removed from storage for use substantially at its stored concentration. In this embodiment, however, a concentrated acid (e.g., pure acid in liquid or solid form, or a highly concentrated aqueous acid solution) is added the concentrated *Bacillus* suspension to provide a higher acid-ammonia neutralization capacity relative to *Bacillus* activity (i.e., similar to Example 7) without substantially diluting the concentrated *Bacillus* suspension. The further acidified, concentrated *Bacillus* suspension is then sprayed directly on surfaces in the area of interest at a surface application rate of about 1 gallon/1000 ft$^2$ (for example at a concentration sufficient to apply at least about $10^6$ or $10^7$ spores/ft$^2$ and/or up to about $10^9$ or $10^{10}$ spores/ft$^2$ to the surface).

Example 11

In another embodiment, the target area of application is in need of a high level of *Bacillus* activity (i.e., similar to Example 4), and the concentrated *Bacillus* suspension containing about $10^9$ spores/ml to about $10^{11}$ spores/ml (or at least about $10^7$, $10^8$, or $10^9$ spores/ml and/or up to about $10^{10}$, $10^{11}$, or $10^{12}$ spores/ml, for example about $10^7$ spores/ml to about $10^{10}$ spores/ml) is removed from storage for use substantially at its stored concentration. In this embodiment, however, concentrated buffer components (e.g., pure buffer salts/acids in liquid or solid form, or a highly concentrated aqueous solution of the same) are added the concentrated *Bacillus* suspension to provide a higher acid-ammonia neutralization capacity relative to *Bacillus* activity (i.e., similar to Example 8) without substantially diluting the concentrated *Bacillus* suspension. The buffered, concentrated *Bacillus* suspension is then sprayed directly on surfaces in the area of interest at a surface application rate of about 1 gallon/1000 ft$^2$ (for example at a concentration sufficient to apply at least about $10^6$ or $10^7$ spores/ft$^2$ and/or up to about $10^9$ or $10^{10}$ spores/ft$^2$ to the surface).

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the Claims attached herein.

What is claimed is:

1. A method for providing a *Bacillus* on a surface, the method comprising:
   (a) providing *Bacillus* spores suspended in a liquid consisting of water and one or more organic acids, wherein the one or more organic acids lower the pH of the liquid so that the *Bacillus* spores are inhibited from germination and growth; and;
   (b) applying the liquid of step (a) to a surface environment either containing ammonia or being capable of generating ammonia, wherein the ammonia neutralizes the one or more organic acids to enable the *Bacillus* spores and provide an enabled *Bacillus* on the surface environment.

2. The method of claim 1, wherein the one or more organic acids consist essentially of acetic acid.

3. The method of claim 2, wherein the acetic acid in the liquid from step (a) is from a fermentation process to produce vinegar.

4. The method of claim 2, wherein the acetic acid in the liquid from step (a) is from a 20% acetic acid vinegar.

5. The method of claim 1, wherein the pH of the liquid in step (a) ranges from about 3.8 to about 4.2.

6. The method of claim 1, wherein the surface environment comprises animal waste comprising an ammonia-generating component.

7. The method of claim 1, wherein the surface environment is an animal enclosure containing animal waste or being susceptible to accumulation of animal waste, the animal waste comprising an ammonia-generating component.

8. The method of claim 7, wherein the animal enclosure is closed to the external environment.

9. The method of claim 7, wherein the animal enclosure is open to the external environment.

10. The method of claim 7, wherein the animal enclosure houses one or more domesticated animals selected from the group consisting of birds, mammals, and combinations thereof.

11. The method of claim 1, wherein the surface environment comprises at least one of a soil surface and a hard surface onto which the liquid in step (a) is applied.

12. The method of claim 11, wherein the surface environment further comprises an animal bedding material on the soil surface or the hard surface.

13. The method of claim 1, wherein the *Bacillus* spores comprise *Bacillus subtilis* that metabolize ammonia.

14. The method of claim 13, wherein the *Bacillus* spores further comprise one or more ammonia-metabolizing *Bacillus* selected from the group consisting of *Bacillus lichenformis, Bacillus pumilis*, and *Bacillus amyloliquefaciens*.

15. The method of claim, wherein the method further comprises at least partially neutralizing the liquid of step (a) with a base.

16. The method of claim 15, wherein the base is selected from the group consisting of sodium bicarbonate, potassium bicarbonate, sodium hydroxide, potassium hydroxide, calcium carbonate, alkaline soil, sodium phosphate (dibasic salt), a glycine salt, and combinations thereof.

17. The method of claim 1, wherein the one or more organic acids in the liquid of step (a) are at a total concentration ranging from 1% to 5%.

18. The method of claim 1, wherein the liquid neutralized by the ammonia and any additional optional base has a pH ranging from about 5 to about 10.

19. A method for providing a *Bacillus* to deodorize an animal waste, the method comprising:
   (a) providing *Bacillus* spores suspended in a liquid consisting of water and one or more organic acids, wherein the one or more organic acids lower the pH of the liquid so that the spores are inhibited from germination and growth, and;
   (b) applying the liquid of step (a) to an animal waste selected from the group consisting of animal feces, animal urine, and combinations thereof, thereby deodorizing the animal waste.

20. The method of claim 19, wherein the one or more organic acids consist essentially of acetic acid.

21. A method for providing a *Bacillus* on a surface, the method comprising:
   (a) providing *Bacillus* spores suspended in a liquid consisting of water and one or more organic acids, wherein the one or more organic acids lower the pH of the liquid so that the *Bacillus* spores are inhibited from germination and growth; and;

(b) applying the liquid of step (a) to agricultural soil or plant material containing ammonia or being capable of generating ammonia, wherein the ammonia neutralizes the one or more organic acids to enable the *Bacillus* spores and provide an enabled *Bacillus* on the surface environment.

* * * * *

UNITED STATES PATENT AND TRADEMARK OFFICE

CERTIFICATE OF CORRECTION

PATENT NO. : 8,722,386 B2
APPLICATION NO. : 12/925371
DATED : May 13, 2014
INVENTOR(S) : Christopher J. Reuter and Steven J. MacKenzie It is certified that error appears in the above-identified patent and that said Letters Patent is hereby corrected as shown below:

On the title page item (57), lines 4-5, Abstract: “The methods comprise suspending the Bacillus spores in a liquid consisting of water. . .” should be -- “The methods comprise suspending the Bacillus spores in a liquid consisting essentially of water. . .” --.

In the Claims:

Column 16, line 35 (claim 15) “The method of claim, wherein. . .” should be -- “The method of claim 1, wherein . . .” --.

Signed and Sealed this
Nineteenth Day of August, 2014

Michelle K. Lee
*Deputy Director of the United States Patent and Trademark Office*